US012748019B2

(12) United States Patent
Meurer et al.

(10) Patent No.: US 12,748,019 B2
(45) Date of Patent: Sep. 29, 2026

(54) INTEGRATED AUTONOMOUS OIL-SLICK SAMPLER AND STORAGE PRESERVATION DEVICE

(71) Applicant: EXXONMOBIL TECHNOLOGY AND ENGINEERING COMPANY, Spring, TX (US)

(72) Inventors: William P. Meurer, Magnolia, TX (US); David T. Wang, Witchita Falls, TX (US); Gregory W. Shipman, Houston, TX (US); Jeffrey D. Spitzenberger, Spring, TX (US); Michael Sutton, Magnolia, TX (US); Jeffrey C. Bridges, Magnolia, TX (US); Paul Moreno, Houston, TX (US)

(73) Assignee: EXXONMOBIL TECHNOLOGY AND ENGINEERING COMPANY, Spring, TX (US)

( * ) Notice: Subject to any disclaimer, the term of this patent is extended or adjusted under 35 U.S.C. 154(b) by 292 days.

(21) Appl. No.: 18/561,480

(22) PCT Filed: Apr. 22, 2022

(86) PCT No.: PCT/US2022/071879

§ 371 (c)(1),
(2) Date: Nov. 16, 2023

(87) PCT Pub. No.: WO2022/251768

PCT Pub. Date: Dec. 1, 2022

(65) Prior Publication Data

US 2024/0248007 A1 Jul. 25, 2024

Related U.S. Application Data

(60) Provisional application No. 63/202,110, filed on May 27, 2021.

(51) Int. Cl.
*G01N 1/10* (2006.01)
*G01N 33/18* (2006.01)
*G01N 1/02* (2006.01)

(52) U.S. Cl.
CPC ........... *G01N 1/10* (2013.01); *G01N 33/1833* (2013.01); *G01N 2001/021* (2013.01); *G01N 2001/028* (2013.01)

(58) Field of Classification Search
CPC ................. G01N 1/10; G01N 33/1833; G01N 2001/021; G01N 2001/028;
(Continued)

(56) References Cited

U.S. PATENT DOCUMENTS

2017/0328814 A1 11/2017 Castendyk et al.
2018/0217029 A1 8/2018 Billings et al.

FOREIGN PATENT DOCUMENTS

JP 2006133206 A * 5/2006
WO WO-2019103209 A1 * 5/2019 ............ B64C 27/12

OTHER PUBLICATIONS

International Search Report and Written Opinion for International Application PCT/US2022/071879 filed Apr. 22, 2022.

* cited by examiner

*Primary Examiner* — Robert R Raevis
(74) *Attorney, Agent, or Firm* — Kevin Davis; WOMBLE BOND DICKINSON (US) LLP

(57) ABSTRACT

An autonomous surface vessel includes an elongate body, and a sampling system operatively coupled to the body and including one or more sampling modules, wherein each sampling module includes a housing including a storage container, a sampling material receivable within the storage container, an actuation system operatively coupled to the sampling material via a lead line, and an end cap operatively coupled to the lead line and matable with an open end of the
(Continued)

storage container. A computer system is in communication with the sampling system to operate the actuation system, wherein each sampling module is actuatable between a stowed state, where the sampling material is received within the storage container and the end cap sealingly engages the open end, and a deployed state, where the end cap is disengaged from the open end and the sampling material is drawn out of the sampling container.

20 Claims, 3 Drawing Sheets

(58) Field of Classification Search
CPC ............ G01N 2001/1025; G01N 1/02; G01N 2001/1031; G01N 1/12; G01V 9/007; B63B 35/00; B63B 2035/007; B63B 2035/008; B63B 35/32
USPC ...... 73/53.01, 64.56, 178 R, 170.29, 170.33, 73/863.01, 863.21, 863.23, 863.25, 73/863.31, 864, 864.31, 864.51, 864.63, 73/864.72, 864.91; 414/137.1, 137.7, 414/137.8, 142.8
See application file for complete search history.

INTEGRATED AUTONOMOUS OIL-SLICK SAMPLER AND STORAGE PRESERVATION DEVICE

CROSS-REFERENCE TO RELATED APPLICATION

This application is a § 371 nationalization of PCT Application Serial No. PCT/US2022/071879, filed Apr. 22, 2022, which claims the benefit of U.S. Provisional Patent Application 63/202,110 filed 27 May 2021 entitled INTEGRATED AUTONOMOUS OIL-SLICK SAMPLER AND STORAGE PRESERVATION DEVICE, the entirety of which is incorporated by reference herein.

FIELD

This disclosure relates generally to the field of hydrocarbon exploration and development and, more particularly, to systems and methods for capturing, storing, and preserving oil samples from the surface of a body of water.

BACKGROUND

As the demand for energy grows globally, hydrocarbon reserves are becoming increasingly difficult to locate and access. As a result, various technologies are utilized to collect measurement data and then model the location of potential hydrocarbon accumulations. The modeling may include factors such as (1) the generation and expulsion of liquid and/or gaseous hydrocarbons from a source rock, (2) migration of hydrocarbons to an accumulation in a reservoir rock, and (3) a trap and a seal to prevent significant leakage of hydrocarbons from the reservoir. The collection of data may be beneficial in modeling potential locations for subsurface hydrocarbon accumulations.

One technique used to determine locations of potential hydrocarbon accumulations includes monitoring hydrocarbon seep locations in offshore oceanic environments. Oil accumulation on the surface of a body of water (e.g. the ocean), sometimes referred to as an "oil slick," may be an indicator of a seafloor hydrocarbon seep location and subsurface hydrocarbon accumulation. Monitoring hydrocarbon seep locations has traditionally been limited to remote monitoring to identify possible waterborne oil locations. This can be performed with satellite or airborne imaging of sea surface slicks. A marine vessel can then be deployed with a manned crew to determine the location of the slick and to obtain samples. Deploying a marine vessel to each location, however, is time consuming and expensive. Moreover, in some cases the deployed marine vessel may not be able to locate the oil slick if the oil slick has dissipated or migrated to a different location due to changes in sea currents and/or wind.

Accordingly, enhanced exploration and sampling techniques is desirable. In particular, exploration techniques used to locate potential seafloor hydrocarbon seeps in a more accurate and cost-effective manner over conventional techniques are desired. These techniques may efficiently obtain samples from waterborne liquid hydrocarbons for indicators of a working hydrocarbon system in exploration areas, which may then be used to enhance basin assessment and to high-grade areas for further exploration.

SUMMARY OF DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

In some embodiments, an autonomous surface vessel is disclosed and includes an elongate body capable of floating on water, and a sampling system operatively coupled to the body and including one or more sampling modules, wherein each sampling module includes a housing including a storage container, a sampling material receivable within the storage container, an actuation system operatively coupled to the sampling material via a lead line, and an end cap operatively coupled to the lead line and matable with an open end of the storage container. The autonomous surface vessel may further include a computer system in communication with the sampling system to operate the actuation system of each sampling module, wherein each sampling module is actuatable between a stowed state, where the sampling material is received within the storage container and the end cap sealingly engages the open end, and a deployed state, where the end cap is disengaged from the open end and the sampling material is drawn out of the sampling container.

In some embodiments, a method of obtaining hydrocarbon samples is disclosed and includes deploying an autonomous surface vessel (ASV) onto a body of water, the ASV including a sampling system having one or more sampling modules, wherein each sampling module includes a housing including a storage container, a sampling material receivable within the storage container, an actuation system operatively coupled to the sampling material via a lead line, and an end cap operatively coupled to the lead line and matable with an open end of the storage container. The method may further include operating the actuation system to deploy the sampling material from the storage container of one of the sampling modules, dragging the sampling material across a surface of the body of water and thereby capturing a sample of a waterborne hydrocarbon on the surface of the body of water, operating the actuation system to retrieve the sampling material back into the storage container, and sealing the sampling material within storage container with the end cap sealingly engaged to the open end.

In some embodiments, a hydrocarbon sampling system is disclosed and includes one or more sampling modules, each sampling module including a housing including a storage container, a sampling material receivable within the storage container, an actuation system operatively coupled to the sampling material via a lead line, and an end cap operatively coupled to the lead line and matable with an open end of the storage container. Each sampling module may be actuatable between a stowed state, where the sampling material is received within the storage container and the end cap sealingly engages the open end, and a deployed state, where the end cap is disengaged from the open end and the sampling material is drawn out of the sampling container.

BRIEF DESCRIPTION OF THE DRAWINGS

The following figures are included to illustrate certain aspects of the disclosure, and should not be viewed as exclusive configurations. The subject matter disclosed is capable of considerable modifications, alterations, combinations, and equivalents in form and function, as will occur to those skilled in the art and having the benefit of this disclosure.

DETAILED DESCRIPTION

Figure 1:
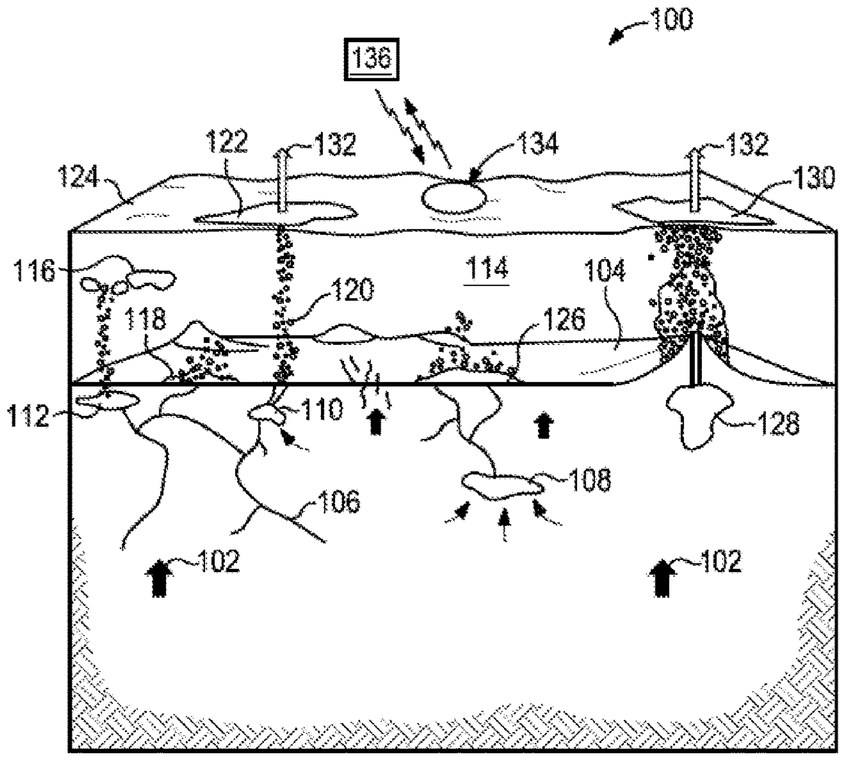
FIG. 1 is a diagram illustrating numerous subsurface sources and migration pathways of hydrocarbons present at or escaping from seeps located on an ocean floor.

The specific embodiments of the present disclosure are described in connection with preferred embodiments. However, to the extent that the following description is specific to a particular embodiment or a particular use of the present disclosure, this is intended to be for exemplary purposes only and simply provides a description of the exemplary embodiments. Accordingly, the disclosure is not limited to the specific embodiments described herein, but rather, it includes all alternatives, modifications, and equivalents falling within the true spirit and scope of the appended claims.

Various terms may be defied herein. To the extent a term used in a claim is not defined herein, it should be given the broadest definition persons in the pertinent art have given that term as reflected in at least one printed publication or issued patent.

As used herein, the term “seep” refers to a natural surface leak of hydrocarbons (e.g., gas and/or oil). The hydrocarbon reaches the surface of the Earth’s crust along fractures, faults, unconformities, or bedding planes, or is exposed by surface erosion into porous rock. The presence of a hydrocarbon seep at the seafloor or surface of the sea indicates that three basic geological conditions critical to petroleum exploration have been fulfilled. First, organic-rich rocks have been deposited and preserved (i.e. source presence); second, the source has been heated and matured (i.e., source maturity); and third, secondary migration has taken place (i.e., hydrocarbon migration from the source location).

Knowledge of the characteristics of naturally seeping hydrocarbons in marine environments can enhance exploration for oil and gas fields. Natural hydrocarbon seeps may result in a thin layer of waterborne liquid hydrocarbons forming on the surface of the body of water, often referred to as “oil slicks”. If oil slick samples are properly collected, stored, and transported to a laboratory, then the samples can be analyzed to determine characteristics of the seeping hydrocarbons. The problem is that naturally occurring waterborne liquid hydrocarbons are often difficult to locate and sample. The conventional practice of sampling an oil slick requires the use of a manned marine vessel on which personnel visually locate the oil slick and then use a hydrophobic fabric or netting to manually collect a sample. This sampling approach is expensive because it involves lengthy deployments to collect samples due to the episodic nature of seeps, expense of personnel to operate the marine vessel, and numerous instances of false positives. Additionally, unfavorable lighting, weather, or sea conditions can make visually locating a slick very difficult. Further still, many of the exploration locations of interest are in frontier areas of the oceans or seas, which are long distances from major ports. The remote nature of these exploration locations increases the cost of the required manned vessel operations.

According to the present disclosure, offshore hydrocarbon identification and exploration may be enhanced by using an autonomous surface vehicle or vessel (ASV) to collect oil slick samples. In some cases, the ASV may be deployed to a region where an oil slick has been previously identified or otherwise sensed. In other cases, or in addition thereto, the ASV may be equipped with instrumentation that allows it to identify the presence of oil on the water surface. As described herein, the ASV may include a sampling system capable of capturing, storing, and preserving oil samples from the surface of a body of water. The sampling system is designed to be mounted on the ASV (or on a micro-barge towed by the ASV) and, when oil is detected, the ASV activates the sampling system and deploys one or more sampling meshes whose high surface area allows them to efficiently scavenge oil. The deployed sampling mesh collects oil from the water surface for a specified amount of time and is then retrieved into an individual storage chamber from which it was deployed. In some embodiments, the storage chamber may be opaque and air-tight, and thereby designed to prevent free circulation of air to the sampling material and also limit oxygen diffusion to the sample.

While the present disclosure is directed primarily to sampling oil (oil slicks) located on the ocean surface, the systems and methods described herein may be equally applicable to sampling other waterborne substances including, but not limited to, pollutants.

FIG. 1 is a schematic diagram 100 illustrating numerous subsurface sources and migration pathways of hydrocarbons 102 present at or escaping from seeps located on an ocean floor 104. Hydrocarbons 102 generated at source rock (not shown) migrate upward through subterranean faults and fractures 106. The migrating hydrocarbons 102 may be trapped in reservoir rock and form a hydrocarbon accumulation, such as a gas 108, a mixture of oil and gas 110, or a gas hydrate accumulation 112. Hydrocarbons 102 seeping from the gas hydrate accumulation 112 may dissolve into methane and higher hydrocarbons (e.g., ethane, propane) in the ocean 114, as shown at 116, or may remain as a gas hydrate on the ocean floor 104, as shown at 118. Alternatively, oil or gas 108 may seep into the ocean 114, as shown at 120, and form waterborne liquid hydrocarbons 122 on the ocean surface 124. In some cases, a bacterial mat 126 may form at a gas seep location, leaking from the gas reservoir 108, and may generate biogenic hydrocarbon gases while degrading thermogenic wet gas. Still another process of hydrocarbon seepage is via a mud volcano 128, which can result in the formation of waterborne liquid hydrocarbons 130 on the ocean surface 124.

Waterborne liquid hydrocarbons 122, 130 are signs of possible subsurface hydrocarbon accumulation and seepage. Gases 132, such as methane, ethane, and propane emitted from the waterborne liquid hydrocarbons 122, 130 can also be a sign of subsurface hydrocarbon accumulation and seepage. The signatures measured from each of these seeps may be analyzed to discriminate between the different origins of hydrocarbons encountered at these seeps. Such analysis may discriminate between hydrocarbons that have migrated directly to the ocean surface 124 without encountering a trap within which they can be accumulated (e.g., a first source) and hydrocarbons that have leaked from a subsurface accumulation (e.g., a second source). If the presence and volume of such a hydrocarbon accumulation can be identified, it is possible the hydrocarbons from such an accumulation can be extracted.

According to embodiments of the present disclosure, an autonomous surface vehicle or vessel (ASV) 134 (depicted in FIG. 1 as a simple oval) may be deployed to collect samples of the waterborne liquid hydrocarbons 122, 130 from the ocean surface 124. The configuration and design of the ASV 134 may vary, depending on the application. In at least one embodiment, the ASV 134 may comprise a catamaran-style unmanned surface vehicle that is capable of traveling at speeds less than 7 knots. One example of the ASV 134 is the Wave Glider available from Liquid Robotics, a Boeing Company, located in Sunnyvale, CA, USA. The Wave Glider is designed to use wave fluctuations for propulsion. Another example of the ASV 134 is the Saildrone available from Saildrone located in Alameda, CA, USA. The Saildrone includes an upright, pivotable sail that captures wind energy for propulsion. Both the Wave Glider and the Saildrone can also include solar panels that capture solar energy to power instrumentation and communication. The captured solar energy can also provide power for a mechanical propulsion system, such as a propeller or the like.

As described in more detail below, the ASV 134 includes a sampling system that includes one or more sampling modules operable to capture, store, and preserve oil samples obtained from the ocean surface 124. Upon locating the waterborne liquid hydrocarbons 122, 130, the ASV 134 activates one or more of the sampling modules to deploy a sampling material configured to scavenge and collect oil from the ocean surface 124. After a period of time, the sampling material is retrieved into an individual storage container from which it was initially deployed, and the storage container is then designed to be sealed to help prevent degradation of the captured sample.

In some embodiments, the ASV 134 may be in communication with one or more remote sensing units 136, such as a satellite, a manned aerial vehicle (e.g., an airplane or helicopter), an unmanned aerial vehicle, or any combination thereof. The remote sensing unit 136 may be configured to collect data regarding the ocean surface 124, identify locations of waterborne liquid hydrocarbons 122, 130, and process the acquired data. The remote sensing unit 136 may then be configured to communicate with the ASV 134 and provide locations (coordinates) where the waterborne liquid hydrocarbons 122, 130 can be found. In some embodiments, the ASV 134 may then be programmed to autonomously travel to the identified locations to obtain samples. In other embodiments, however, the locations of the waterborne liquid hydrocarbons 122, 130 may instead be provided to a central command center or the like and an operator may have the option to manually direct the ASV 134 to travel to the identified locations to obtain samples.

Figure 2:
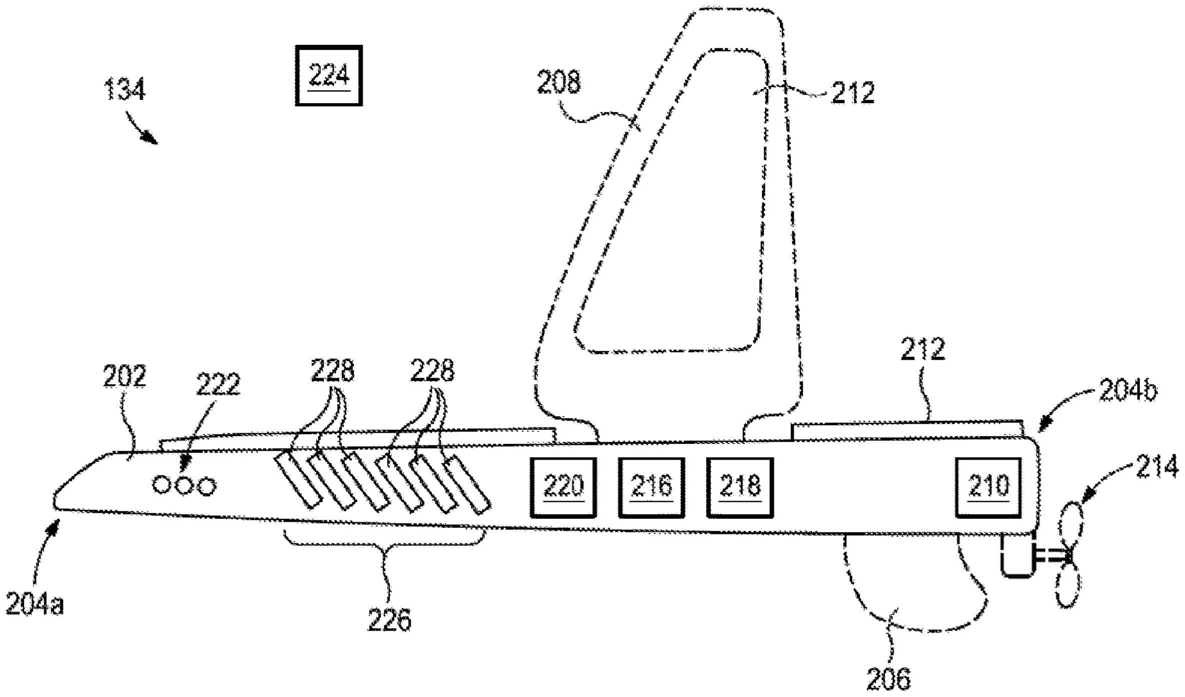
FIG. 2 is a schematic side view of an example of the autonomous surface vehicle of FIG. 1, according to one or more embodiments of the present disclosure.

FIG. 2 is a schematic side view of an example of the ASV 134, according to one or more embodiments of the present disclosure. While the ASV 134 is depicted in FIG. 2 as having a particular shape and design, the configuration of the ASV 134 may vary without departing from the scope of the disclosure. As illustrated, the ASV 134 has an elongate body 202 having a first end or "bow" 204*a* and a second end or "stern" 204*b* opposite the bow 204*a*. In some embodiments, the ASV 134 may have a keel 206 (shown in dashed lines) arranged at or near the stern 202*b* to help guide the steering of the ASV 134 and stabilize the body 202. Moreover, in some embodiments, the ASV 134 may include a sail 208 (shown in dashed lines) configured to capture wind energy for propulsion.

The ASV 134 may include a power module 210 configured to provide electrical power to the various onboard electrical equipment and modules of the ASV 134. The power module 210 may comprise any device or mechanism capable of generating or storing electrical power. The power module 210 may include, but is not limited to, one or more batteries, one or more fuel cells, a motor, solar powered equipment, wave powered equipment (e.g., fins and springs that capture wave energy), or any combination thereof.

In some embodiments, as illustrated, the ASV 134 may include one or more solar panels 212 mounted to the body 202 and used to capture and convert solar energy into electricity. In at least one embodiment, as illustrated, a solar panel 212 may also be installed on the sail 208. In embodiments where the power module 210 comprises one or more batteries, the solar panels 212 may be configured to charge the batteries, which provide electrical power to the onboard electrical equipment and modules. Alternatively, the solar panels 212 may provide electrical power directly to one or more of the onboard electrical equipment and modules, without departing from the scope of the disclosure.

The ASV 134 may also include a mechanical propulsion system 214 (shown in dashed lines), which may be powered by the power module 210. In the illustrated embodiment, the mechanical propulsion system 214 includes a motor coupled to a propeller assembly via a shaft, but could alternatively comprise other types of devices or mechanisms configured to propel the ASV 134 across a body of water (e.g., the ocean 114).

The ASV 134 may include a computer system 216 configured and otherwise programmed to operate the ASV 134 and the various onboard electrical equipment and modules. As indicated above, the ASV 134 may be configured for autonomous control or may be remotely operated, and in either case the computer system 216 may facilitate operation of the ASV 134. The computer system 216 may be in communication with a communications module 218 configured to facilitate remote communication with various entities or modules, such as the remote sensing unit 136 (FIG. 1) or a central command center. In some embodiments, an operator may remotely control the ASV 134 by communicating with the ASV 134 via the communications module 218.

The ASV 134 may further include a measurement module 220 in communication with the computer system 216 and configured to obtain measurement data and transmit that data to the computer system 216 for processing. In some embodiments, the measurement module 220 may include or otherwise be in communication with one or more sensors 222 operable to detect and locate the waterborne liquid hydrocarbons 122, 130 (FIG. 1). In at least one embodiment, the sensor(s) 222 may be arranged at or near the bow 204*a* and on one or both sides of the ASV 134. This may prove advantageous in being able to analyze the ocean surface 124 (FIG. 1) and detect oil slicks before being disrupted by the wake (turbulence) of the moving ASV 134. One or more of the sensors 222 may comprise a hydrocarbon sensor, such as a flourometer, which may be used to identify the hydrocarbons and analyze the water to detect certain wavelengths. The use of the flourometer may include pumping surface compounds from the ocean surface 124 (sea water and hydrocarbons) through the flourometer to identify hydrocarbons. The analysis of certain wavelengths may include receiving and analyzing signals from the ocean surface 124 to detect certain wavelengths, which are utilized to identify hydrocarbons.

In other embodiments, the measurement module 220 may include or otherwise operate an aerial vehicle 224 deployable from the ASV 134 to travel in the air above the ASV 134 and analyze the ocean surface 124 (FIG. 1) at an elevated position. In some embodiments, the aerial vehicle 224 may comprise a balloon tethered to the ASV 134 via an umbilical and including various sensors configured to detect and locate the waterborne liquid hydrocarbons 122, 130 and communicate data with the measurement module 220. In other embodiments, the aerial vehicle 224 may comprise an unmanned aerial vehicle (UAV) or drone that may be launched from the ASV 134 and include cameras or other sensors to identify hydrocarbons over a broad area. In such embodiments, the UAV may communicate measurement data to the measurement module 220 via wireless communication, or the UAV may otherwise be tethered to the ASV 134 via an umbilical. The aerial vehicle 224 may include infrared and visible light detection components capable of obtaining infrared and visible light images for the region around the ASV 134 and analyzing the infrared and visible light images to identify hydrocarbons. The aerial vehicle 224 may further include active ultra-violet sensors that are configured to excite aromatic compounds in hydrocarbons and to detect resulting fluorescence emissions from the surface of the slick. The aerial vehicle 224 may also include visible and infrared light cameras that can be used to investigate larger areas around the ASV 134 to locate slicks.

In other embodiments, the measurement module 220 may be configured to obtain other measurement data, such as camera images, temperature data, mass spectrometric data, conductivity data, fluorometric data, and/or polarization data, for example. The data can be in the format of images, raw data with specific format for the component, text files, and/or any combination of the different types. Other sensors 222 may include functionality to provide chemical specificity of applied sensors (e.g., mass spectrometry). These sensors 222 may discriminate thermogenic hydrocarbons, which may be preferred, from biogenic hydrocarbons and may determine whether the seep is associated with gas, oil, or a combination of gas and oil.

The ASV 134 may further include a sampling system 226 configured to capture, store, and preserve oil samples obtained from the ocean surface 124 (FIG. 1). The sampling system 226 may include one or more sampling modules 228 operable (activatable) to deploy a sampling material designed to scavenge (capture) oil from the ocean surface 124. The oil-laden sampling material is subsequently retrieved into an individual storage container from which it was deployed, and the storage container is sealed to help prevent degradation of the sample. While six sampling modules 228 are depicted in FIG. 2, more or less than six may be included in the sampling system 226. In some embodiments, for example, the sampling system 226 may have at least twenty sampling modules 228 and may have as many as two hundred, without departing from the scope of the disclosure.

While the sampling modules 228 are depicted in FIG. 2 as being all located in a single, grouped location, the modules 228 may alternatively be placed in any location about the body 202 of the ASV 134, without departing from the scope of the disclosure. Indeed, the sampling system 226 and modules 228 may be secured to any surface of the ASV 134 that allows the sampling modules 228 to successfully deploy and retrieve the sampling material. In the illustrated embodiment, the sampling system 226 is depicted as being secured to a side of the body 202, but could alternatively be secured to the top or at or near the stern 204*b* of the body 202, without departing from the scope of the disclosure. In other embodiments, however, the sampling system 226 may be located on a boom of an outrigger system or on a separate vessel towed behind the ASV 134, as discussed herein.

In some embodiments, once oil is detected via operation of the measurement system 220, the computer system 216 may communicate with the sampling system 226 and trigger activation of one or more of the sampling modules 228. In such embodiments, the computer system 216 may be programmed to activate sampling modules 228 based on oil detection or on a timed basis for regular sampling. Moreover, the computer system 216 may be programmed to allow the sampling material to scavenge the ocean surface 124 (FIG. 1) for oil for a predetermined time period, which can comprise seconds, minutes, hours, or days. In other embodiments, however, a remote operator may be able to remotely activate the sampling system 226 on demand by communicating with the computer system 216 via the communications module 218. In such embodiments, the duration of the sampling can also be determined on demand or for a predetermined time.

Figure 3A:
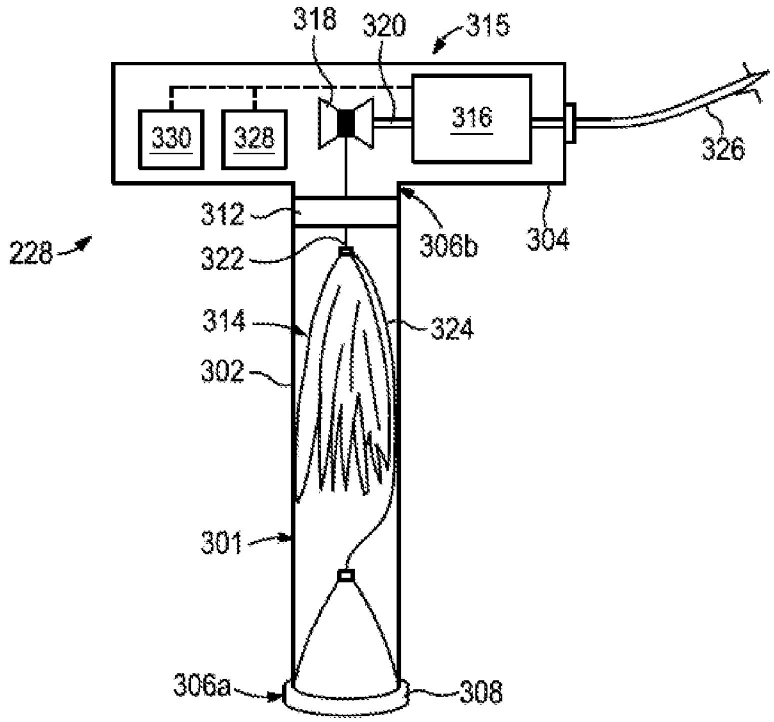
FIGS. 3A and 3B are schematic views of an example sampling module, according to one or more embodiments.
Figure 3B:
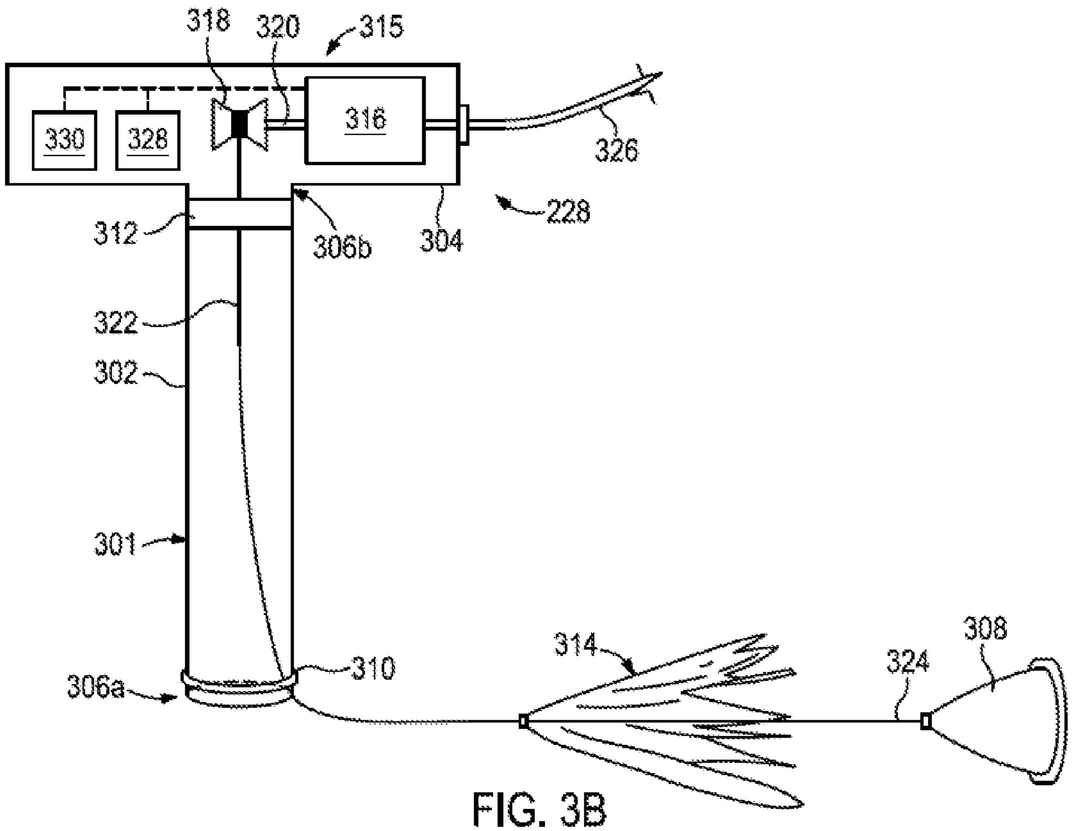

FIGS. 3A and 3B are schematic views of an example sampling module 228, according to one or more embodiments. More specifically, FIG. 3A depicts the sampling module 228 in a first or "stowed" state, and FIG. 3B depicts the sampling module 228 in a second or "deployed" state. The computer system 216 may communicate with the sampling module 228 to cause the sampling module 228 to transition between the stowed and deployed states, as needed. The stowed state can refer to 1) pre-deployment (i.e., prior to being actuated to the deployed state) or 2) following operation in the deployed state where the sampling module 228 is returned to its initial configuration to store an acquired sample.

The sampling module 228 is depicted in FIGS. 3A-3B as exhibiting a specific shape, design, and configuration, but the sampling module 228 may alternatively include other shapes, designs, and configurations and still perform the same primary functions, without departing from the scope of the disclosure. Indeed, the design of the sampling module 228 and its electronics may vary depending on the type of ASV 134 on which it is deployed. As will be appreciated, the form factor of the sampling module 228 may be modified to best accommodate placement on the ASV 134. Accordingly, the particular shape, design, and configuration of the sampling module 228 shown in FIGS. 3A-3B is provided merely for example purposes, and should not be considered limiting to the scope of the disclosure.

As illustrated, the sampling module 228 includes a housing 301 that includes a storage container 302 and a head compartment 304 operatively coupled to or extending from the storage container 302. The storage container 302 may comprise a generally hollow cylindrical or tubular structure having a first or "bottom" end 306*a* and a second or "top" end 306*b* opposite the first end 306*a*. In some embodiments, as illustrated, the storage container 302 may exhibit a circular cross-section, but may alternatively exhibit other cross-sectional shapes, such as polygonal, oval, ovoid, or any combination thereof.

In some embodiments, the sampling module 228 may include an end cap 308 configured to mate with and sealingly engage the first end 306*a* of the storage container 302. The end cap 308 may be made of a pliable material, such as an elastomer or a polymer capable of forming a sealed interface when brought into contact with the first end 306*a*. In other embodiments, however, one or more gaskets 310 (see FIG. 3B) may be arranged at the first and 306*a* and configured to facilitate a sealed interface between the end cap 308 and the first end 306*a*. The gasket 310 may comprise, for example, an O-ring or another type of annular seal. In the illustrated embodiment, the gasket 310 is depicted as being arranged on the outside of the storage container 302, but could alternatively be arranged within the interior of the storage container 302 or arranged on (e.g., overmolded onto) the bottom of the first end 306*a*, without departing from the scope of the disclosure. In yet other embodiments, the gasket 310 may be carried by the end cap 308 and arranged to sealingly engage any surface (interior, exterior, end, etc.) of the first end 306*a* of the storage container 302. In such embodiments, the gasket 310 may form an integral part of the end cap 308 or may otherwise comprise a separate component part carried therewith.

In some embodiments, a container seal 312 may be arranged within the interior of the storage container 302 at or near the second end 306*b*. The container seal 312 may be made of a material capable of facilitating a sealed interface within the storage container 302. When the end cap 308 is mated with and sealingly engaged at the first end 306*a*, the combination of the end cap 308 and the container seal 312 may hermetically seal the interior of the storage container 302 so that no fluids (gas or liquid) are able to migrate in or out of the storage container 302 in either direction. In other embodiments, however, the container seal 312 may be omitted and the head compartment 304 may alternatively comprise a sealed container (capsule) capable of holding a hermetic seal within the interior of the sampling module 228 when the end cap 308 is mated with and sealingly engaged at the first end 306*a*.

The storage container 302 may be capable of receiving and storing a sampling material 314 within the interior between the first and second ends 306*a,b*. In some embodiments, the sampling material 314 may comprise a mesh or screening fabric made of an oleophilic and hydrophobic material. The sampling material 314 may be made of an organic polymer such as, but not limited to, polytetrafluoroethylene (PTFE or TEFLON®), high-density polypropylene, low-density polypropylene, polyethylene, high density polyethylene (HDPE), low density polyethylene (LDPE), or any combination thereof. In other embodiments, the sampling material 314 may be made of a metal, such as steel wool, brass, copper, or any alloy thereof.

The sampling material 314 may comprise a multi-strand, finely woven mesh or fabric that results in high surface-to-volume ratio, which may be advantageous in capturing hydrocarbon molecules. The hole spacing of the sampling material 314 may be about 150-200 microns, for example. In other embodiments, however, the hole spacing of the sampling material 314 could be as small as 10-50 microns, or as coarse as 350 microns or more. The fiber diameter of the fabric can also be as fine 10 microns or range up to nearly 100 microns. These strands may be are twisted to make the mesh whose thickness varies between 50 microns to about 350 microns. In some embodiments, the mesh or screening fabric of the sampling material 314 may have a thickness of about 0.1 millimeters (mm) to about 0.7 mm, or more preferably about 0.3 mm. As will be appreciated, material selection and sizing may be optimized based on mission objectives, costs, and environmental concerns (e.g., algae clogging up small meshes).

As described in more detail below, the sampling material 314 may be deployed from the sampling container 302 and then be dragged through the waterborne liquid hydrocarbons 122, 130 (FIG. 1) based on the sampling pattern of the ASV 134 (FIGS. 1 and 2) before being retrieved back into the sampling container 302. In some embodiments, the sampling material 314 may be buoyant or close to buoyant when in the water (e.g., sea or ocean water), and thus able to stay on the ocean surface 124 (FIG. 1).

As indicated above, the head compartment 304 may be operatively coupled to or otherwise extend from the storage container 302. In some embodiments, for example, the head compartment may comprise a separate component structure operatively coupled, either directly or indirectly, to the storage container 302 at the second end 306*b*. In other embodiments, however, the head compartment 304 may form an integral part or extension of the storage container 302. In such embodiments, the housing 301 of the sampling module 228 may comprise a monolithic structure.

The head compartment 304 may provide or define an interior sized to receive various devices and modules used to operate the sampling module 228. In the illustrated embodiment, the head compartment 304 may house an actuation system 315 operable to transition the sampling module 228 between the stowed configuration, as shown in FIG. 3A, and the deployed configuration, as shown in FIG. 3B.

In some embodiments the actuation system 315 may include a motor 316 and a spool 318 operatively coupled to the motor 316 via a drive shaft 320. A lead line 322 may be wound around the spool 318 and coupled to the sampling material 314. In at least one embodiment, as illustrated, the lead line 322 may extend through the container seal 312 to be coupled to the sampling material 314. Actuation of the motor 316 causes the drive shaft 320 to rotate and thereby rotate the spool 318 in the same direction. Depending on the rotational direction of the spool 318, the lead line 322 is either progressively wound onto the spool 318 or discharged (paid out) from the spool 318, and movement of the lead line 322 correspondingly acts on the sampling material 314 to either draw the sampling material 314 into the sampling container 302 or allow the sampling material 314 to be deployed from the interior of the sampling container 302. In some embodiments, the motor 316 may comprise a finely geared motor that allows the lead line 322 to be progressively wound onto or discharged from the spool 318 in small increments, if desired.

While the actuation system 315 is depicted in FIGS. 3A-3B as including the motor 316 and the spool 318, it is contemplated herein that the actuation system 315 may comprise any other device or mechanism capable of deploying the sampling material 314 from the sampling container 302 and subsequently retrieving (drawing) the sampling material back into the sampling container 302, without departing from the scope of the disclosure. Those skilled in the art will readily appreciate the various configurations of mechanisms and devices that are equally capable of drawing in and paying out the lead line 322, and thereby manipulating the position of the sampling material 314. Accordingly, actuation system 315 shown in FIGS. 3A-3B are provided merely for example purposes, and should not be considered limiting to the scope of the disclosure.

In some embodiments, a cap line 324 operatively couples the end cap 308 to the sampling material 314 and the lead line 322. In some embodiments, the cap line 324 is an extension of the lead line 322, but could alternatively form a separate line structure coupled to the lead line 322 and extending therefrom. The cap line 324 helps keep the end cap 308 operatively connected to the sampling material 314 such that the end cap 308 and the sampling material 314 are able to be deployed out of or stowed within the sampling container 302 as a coupled assembly.

In some embodiments, the motor 316 may be in communication with the computer system 216 (FIG. 2) and the power module 210 (FIG. 2) via a direct communication and power line 326. When it is desired to operate the motor 316, power and communication signals are provided to the motor 316 via the direct communication and power line 326. In other embodiments, however, the communication and power line 326 may be omitted and the motor 316 may be instead be in communication with an onboard computer system 328 and an onboard power source 330. The onboard computer system 328 may communicate with the computer system 216, but may also include communications capabilities that allow an operator to communicate and operate the sampling module 228 remotely. The onboard power source 330 may be configured to provide electrical power to operate the motor 316 and may include one or more batteries or fuel cells. When it is desired to operate the motor 316, power and communication signals are provided to the motor 316 from the onboard computer system 328 and the onboard power source 330.

In some embodiments, as illustrated, the onboard computer system 328 and the onboard power source 330 may be arranged within housing 301 and, more particularly, within the head compartment 304. In other embodiments, however, one or both of the onboard computer system 328 and the onboard power source 330 may form part of the sampling system 226 (FIG. 2) generally and may be configured to facilitate operation of multiple sampling modules 228.

Example operation of the sampling module 228 is now provided. As indicated above, the sampling module 228 may be activated via command signals derived from the computer system 216 (FIG. 2) or alternatively the onboard computer system 318. The command signals may be 1) pre-programmed commands based on the detection of oil, 2) pre-programmed commands based a predetermined sampling schedule, or 3) real-time, on demand commands based on operator input. When the sampling module 228 is activated, the motor 316 rotates the spool 318 to enable the lead line 322 to be discharged (unwound or paid out) from the spool 318. In at least one embodiment, as the lead line 322 is paid out, gravitational forces acting on the end cap 308 allow the end cap 308 to dislodge from the first end 306*a* of the sampling container 302. The weight of the end cap 308 pulls on the cap line 324, which correspondingly acts on and urges the sampling material 314 out of the sampling container 302 as additional lead line 322 is dispensed from the spool 318.

Once the end cap 308 and the sampling material 314 are deployed from the sampling container 302, as shown in FIG. 3B, the sampling material 314 is able to contact the surface of the water (e.g., the ocean surface 124 of FIG. 1). As the ASV 134 (FIGS. 1 and 2) moves forward, the sampling material 314 and the end cap 308 are dragged along the surface of the water. In some embodiments, the end cap 308 may be made of a buoyant material. In such embodiments, the end cap 308 may be made of an elastomer that is positively buoyant in water, for example, and makes a seal. Alternatively, the end cap 308 may be made of a composite material that integrates an elastomer for the seal with a lower density, more rigid plastic for added buoyancy. In at least one embodiment, the end cap 308 may include one or more air pockets that promote buoyancy. In such embodiments, the end cap 308 may be made of a material that is not buoyant in water, but the air pockets may make the end cap 308 buoyant. In yet other embodiments, the end cap 308 may be entirely rigid and buoyant, and the sealing at the first end 306*a* may be accomplished using the gasket 310, for example.

The lead line 322 helps to maintain the front of the sampling material 314 at the surface of the water, and the buoyancy of the end cap 308 trailing behind helps to maintain the tail of the sampling material 314 at the surface of the water. Between the lead line 322, the cap line 324, and the end cap 308, there may be enough tension to keep the entirety of the sampling material 314 at the water surface during sampling. Moreover, as indicated above in some embodiments, the sampling material 314 itself may be buoyant.

After the sampling material 314 has been able to collect hydrocarbon samples for a predetermined amount of time, or whenever an operator wishes to end the sampling procedure, the sampling module 228 may once again be activated to retrieve the sampling material 314 back into the sampling container 302. More specifically, command signals derived from the computer system 216 (FIG. 2) or the onboard computer system 318 may cause the motor 316 to rotate the spool 318 in the opposite angular direction and thereby progressively wind the lead line 322 back onto the spool 318. As the lead line 322 is wound back onto the spool 318, the sampling material 314 is drawn back into the sampling container 302 until the end cap 308 sealingly engages the first end 306*a* of the sampling container 302. In some embodiments, as illustrated, the end cap 308 may exhibit a generally conical shape that can be easily received into the open first end 306*a* of the sampling container 302.

In some embodiments, the lead line 322, including the cap line 324, may be elastic, and the motor 316 may wind the lead line 322 until a predetermined tension is achieved in the lead line 322, at which point the motor 316 ceases operation. The tension built up in the lead line 322 may be sufficient to drive the end cap 308 into sealed engagement with the first end 306*a* of the sampling container 302. Moreover, in some embodiments, the motor 316 may prevent backdriving, which prevents the spool 318 from inadvertently unwinding and releasing the tension on the end cap 308, which helps maintain the sealed interface between the end cap 308 and the first end 306*a* of the sampling container 302.

According to embodiments of the present disclosure, when the end cap 308 is pulled back into place and sealingly engages the first end 306*a* of the sampling container 302, a hermetic seal is generated that precludes oxygen from entering the sampling container 302. Consequently, the hydrocarbon sample collected on the sampling material 314 will be sealed within the sampling container 302. Based on experimental results, limiting the amount of oxygen present in stored oil samples may be critical for preservation. More specifically, aerobic, single-celled microorganisms are often present in stored oil samples and they generate energy by feeding on the carbon-hydrogen bonds of interest (i.e., biomarkers that provide information about source rock, the level of thermal maturity, the chemistry of the source rock, etc.). If the activity of these microorganisms is not hindered or impeded, hydrocarbon molecules of interest may be consumed, and the sampling process may be frustrated or otherwise adversely affected.

Since these microorganisms are commonly aerobic by nature, they use oxygen as a way to break the hydrocarbon bonds, and produce $CO_2$ and water as a byproduct. One way to stop the microorganisms from consuming hydrocarbon molecules of interest is to limit the supply of oxygen. Accordingly, with the sampling material 314 being hermetically sealed, it is only a matter of time until the oxygen has been consumed, at which point consumption (degradation) of the hydrocarbon molecules of interest by the by microorganisms ceases.

Since oxygen diffusivity into the interior of the sampling module 228 may be a key factor in limiting sample degradation, some or all of the component parts of the sampling module 228 may be made of materials exhibiting low oxygen permeability coefficients. In some embodiments, for example, the housing 301 of the sampling module 228 (e.g., the sampling container 302 and/or the compartment head 304) may be made of a material that exhibits an oxygen permeability coefficient of 5 barrer or less. Moreover, the end cap 308 may be made of a material that exhibits an oxygen permeability coefficient of 10 barrer or less. The sampling container 302, the compartment head 304, and the end cap 308 may be made of a plastic, for example, such as a thermoplastic or a thermoset. Furthermore, the gasket 310 may be made of a material that exhibits an oxygen permeability coefficient of 20 barrer or less, and in embodiments including the container seal 312, the container seal 312 may be made of a material that exhibits an oxygen permeability coefficient of 10 barrer or less. The gasket 310 and the container seal 312 may each be made of an elastomer, for example, and in some embodiments, the end cap 308 may also be made of an elastomer.

In some embodiments, various parts of the sampling module 228 may be made of an opaque material and provide resistance to breakdown under ultra-violet (UV) exposure. The opaque material may prove advantageous since UV energy can degrade oils. Moreover, various parts of the sampling module 228 may be made of a material that provides resistance to breakdown when exposed to salt water. As with any marine deployment, the various parts of the sampling module 228 should be hardened to impacts of salt water, for example.

Figure 4:
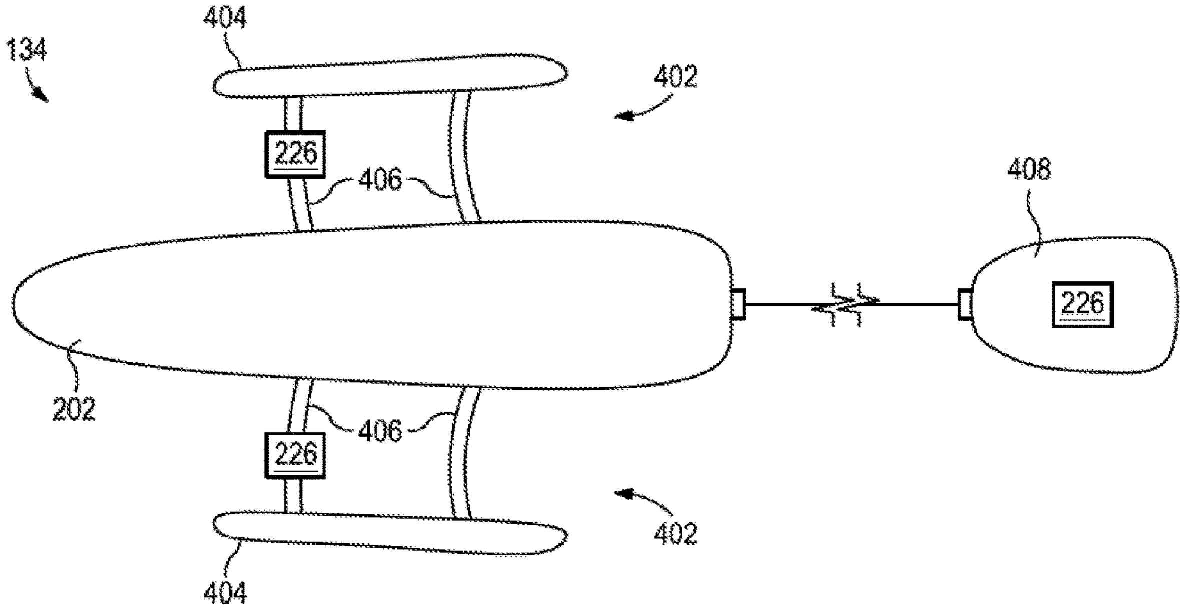
FIG. 4 is a top view of the autonomous surface vehicle of FIG. 2, according to one or more additional embodiments.

FIG. 4 is a top view of the ASV 134, according to one or more additional embodiments. In the illustrated embodiment, the ASV 134 can include one or more outriggers 402 (two shown). The outriggers 402 may be arranged on one or both sides of the body 202 to the ASV 134 and may include a float 404 and one or more booms 406 extending between the float 404 and the body 202. The outriggers 402 may help to remove any bow effect of cutting through oily water, and may also help balance the drag on each side of the ASV 134 and thereby enhance roll stability.

In some embodiments, the sampling system 226 or one or more sampling modules 228 (FIG. 2) from the sampling system 226 may be operatively coupled to the body 302 of the ASV 134 by being mounted to one or more of the booms 406. As used herein, the term "operatively coupled" refers to a direct or indirect coupled engagement. Accordingly, operatively coupling the sampling system 226 to a boom 406 effectively couples the sampling system 226 to the body 302 of the ASV 134.

In some embodiments, as illustrated, the sampling system 226 or one or more sampling modules 228 (FIG. 2) from the sampling system 226 may alternatively, or in addition thereto, but arranged on a micro-barge 408 towed by the ASV. In such embodiments, an umbilical 410 may extend between the ASV 134 and the sampling system 226 to ensure power and communication is provided to the sampling system 226. In other embodiments, however, the sampling system 226 may include its own onboard power and communication systems, without departing from the scope of the disclosure.

Figure 5:
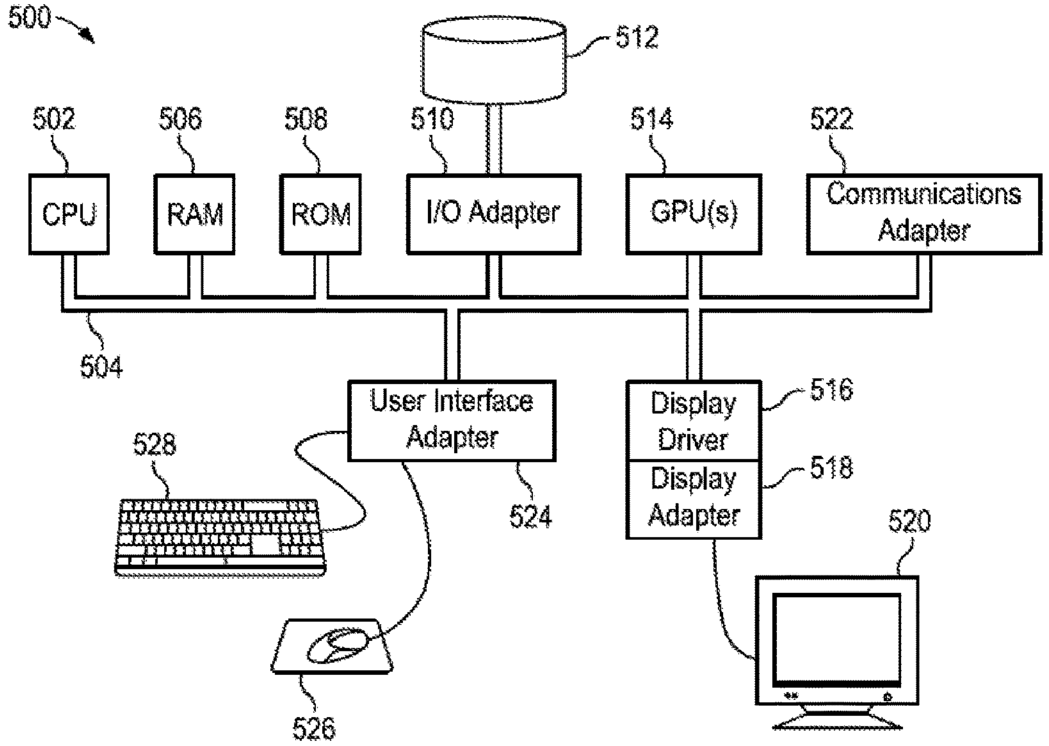
FIG. 5 is a block diagram of a computer system that may be used to perform any of the methods disclosed herein.

FIG. 5 is a block diagram of a computer system 500 that may be used to perform any of the methods disclosed herein. The computer system 500 may be representative of one or both of the computer systems 216 and 328 of FIGS. 2 and 3A-3B, respectively. A central processing unit (CPU) 502 is coupled to a system bus 504. The CPU 502 may be any general-purpose CPU, although other types of architectures of CPU 502 (or other components of exemplary system 500) may be used as long as CPU 502 (and other components of system 500) supports the inventive operations as described herein. The CPU 502 may execute the various logical instructions according to disclosed aspects and methodologies. For example, the CPU 502 may execute machine-level instructions for performing processing according to aspects and methodologies disclosed herein.

The computer system 500 may also include computer components such as a random access memory (RAM) 506, which may be SRAM, DRAM, SDRAM, or the like. The computer system 500 may also include read-only memory (ROM) 508, which may be PROM, EPROM, EEPROM, or the like. RAM 506 and ROM 508 hold user and system data and programs, as is known in the art. The computer system 500 may also include an input/output (I/O) adapter 510, a communications adapter 522, a user interface adapter 524, and a display adapter 518. The I/O adapter 510, the user interface adapter 524, and/or communications adapter 512 may, in certain aspects and techniques, enable a user to interact with computer system 500 to input information.

The I/O adapter 510 preferably connects a storage device (s) 512, such as one or more of hard drive, compact disc (CD) drive, floppy disk drive, tape drive, etc. to the computer system 500. The storage device(s) 512 may be used when RAM 506 is insufficient for the memory requirements associated with storing data for operations of embodiments of the present techniques. The data storage of the computer system 500 may be used for storing information and/or other data used or generated as disclosed herein. The communications adapter 522 may couple the computer system 500 to a network (not shown), which may enable information to be input to and/or output from system 500 via the network (for example, a wide-area network, a local-area network, a wireless network, any combination of the foregoing).

The user interface adapter 524 couples user input devices, such as a keyboard 528, a pointing device 526, and the like, to the computer system 500. The display adapter 518 is driven by the CPU 502 to control, through a display driver 516, the display on a display device 520. Information and/or representations of one or more 2D canvases and one or more 3D windows may be displayed, according to disclosed aspects and methodologies.

The architecture of the computer system 500 may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to the embodiments.

In one or more embodiments, the methods described herein may be implemented in machine-readable logic, such that a set of instructions or code that, when executed, performs automated sampling operations from memory. That is, the ASV 134 (FIGS. 1, 2, and 4) may be configured to operate in an autonomous mode. As an example, operating in an autonomous manner may include navigating and sampling the potential waterborne liquid hydrocarbons without the interaction of an operator. In such configurations, the ASV 134 may include a control unit, which may be the computer system 500, as noted in FIG. 5. During the deployment, the ASV 134 may navigate toward targeted locations or may navigate along a specific search pattern. To navigate, the ASV 134 may utilize navigation components, which may include one or more propulsion components, one or more steering components and the like. The one or more propulsion components may include a motor coupled to one or more batteries and coupled to a propeller assembly, via a shaft, for example, as is known in the art. The propeller assembly may be utilized to move fluid in a manner to move the unmanned vehicle relative to the body of water. The navigation components may utilize sensors or other monitoring devices to obtain navigation data. The navigation data may include different types of navigational information, such as inertial motion unit (IMU), global positioning system information, compass information, depth sensor information, obstacle detection information, SONAR information, propeller speed information, seafloor map information, and/or other information associated with the navigation of the unmanned vehicle. The deployment may also include inserting certain equipment (e.g., certain monitoring components) into the ASV 134 for use in sampling operations. As an example, the deployment may include lowering the ASV 134 from the deck of a marine vessel into the body of water or dropping the unmanned vehicle into the body of water from an airborne vehicle.

The control unit may manage the operations of the communication components, sampling components, hydrocarbon detection and identification components, power components and propulsion components. The control unit may be configured to direct the navigation components to follow a direct trajectory to a target location and/or follow one or more search patterns. This may also involve adjusting operational parameters and/or settings to control the speed and direction. Further, the control unit may adjust the operation of the hydrocarbon detection and identification components. That is, the control unit may have the hydrocarbon detection and identification components perform the detection operations in a specific sequence. Further, the control unit may also control the sampling operations. The sampling operations may be controlled by the control unit to obtain a certain number of samples, the duration the samples are in contact with the hydrocarbons on the body of water and other such operational aspects.

Unless indicated to the contrary, the numerical parameters set forth in the current specification and attached claims are approximations that may vary depending upon the desired properties sought to be obtained by the incarnations of the present inventions. At the very least, and not as an attempt to limit the application of the doctrine of equivalents to the scope of the claim, each numerical parameter should at least be construed in light of the number of reported significant digits and by applying ordinary rounding techniques.

One or more illustrative incarnations incorporating one or more invention elements are presented herein. Not all features of a physical implementation are described or shown in this application for the sake of clarity. It is understood that in the development of a physical embodiment incorporating one or more elements of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While systems and methods are described herein in terms of "comprising" various components or steps, the systems and methods can also "consist essentially of" or "consist of" the various components and steps.

Therefore, the present invention is well adapted to attain the ends and advantages mentioned as well as those that are inherent therein. The particular examples and configurations disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative examples disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. An autonomous surface vessel, comprising:

an elongate body capable of floating on water;

a device configured to identify one or more locations of hydrocarbons floating on the water;

a sampling system operatively coupled to the body and including at least one sampling device, wherein the at least one sampling device includes:

a housing including a storage container;

a sampling material receivable within the storage container;

an actuation system operatively coupled to the sampling material via a lead line; and an end cap operatively coupled to the lead line and matable with an open end of the storage container; and a computer system in communication with the sampling system to control operation of the autonomous surface vessel in order to operate the actuation system of the at least one sampling device to obtain one or more samples at the one or more locations of the hydrocarbons, wherein at least one sampling device is actuatable between a stowed state, where the sampling material is received within the storage container and the end cap sealingly engages the open end, and a deployed state, where the end cap is disengaged from the open end and the sampling material is drawn out of the storage container.

2. The autonomous surface vessel of claim 1, wherein the end cap is configured to hermetically seal the at least one sampling device in order to preclude oxygen from entering the storage container so that the sampling material is hermetically sealed within the storage container when the at least one sampling device is in the stowed state.

3. The autonomous surface vessel of claim 1, wherein the housing is made of a material that exhibits an oxygen permeability coefficient of 5 barrer or less, wherein the end cap is made of a material that exhibits an oxygen permeability coefficient of 10 barrer or less;

wherein the at least one sampling device further includes one or more gaskets that facilitate a sealed interface between the end cap and the open end; and wherein the one or more gaskets are made of a material that exhibits an oxygen permeability coefficient of 20 barrer or less.

4. The autonomous surface vessel of claim 1, wherein the sampling material is buoyant in water; and wherein the sampling material comprises a mesh or screening fabric made of an oleophilic and hydrophobic material.

5. The autonomous surface vessel of claim 4, wherein the mesh or the screening fabric has a thickness of about 0.1 millimeters to about 0.7 millimeters.

6. The autonomous surface vessel of claim 1, wherein the sampling material is made of:

an organic polymer selected from the group consisting of polytetrafluoroethylene, high-density polypropylene, low-density polypropylene, polyethylene, and any combination thereof; or a metal selected from the group consisting of steel wool, brass, copper, and any alloy thereof.

7. The autonomous surface vessel of claim 1, further comprising a measurement device mounted to the body and in communication with the computer system, the measurement device including one or more sensors operable to detect and locate waterborne liquid hydrocarbons on a water surface; and wherein the measurement device includes an aerial vehicle deployable from the body to travel above the body, wherein at least one of the one or more sensors is mounted to the aerial vehicle.

8. The autonomous surface vessel of claim 1, further comprising a communications device mounted to the body and in communication with the computer system, wherein the communications device facilitates remote communication between the computer system and an operator for remote operation of the sampling system.

9. The autonomous surface vessel of claim 1, wherein the actuation system comprises a motor and a spool operatively coupled to the motor via a drive shaft, and wherein the lead line is wound around the spool and actuation of the motor progressively winds the lead line onto the spool or feeds the lead line from the spool and thereby acts on the sampling material and the end cap;

wherein the at least one sampling device further comprises an onboard power source that powers the actuation system; and wherein the housing is made of an opaque material.

10. The autonomous surface vessel of claim 1, further comprising;

an outrigger arranged on at least one side of the body, the outrigger including a float and a boom extending between the float and the body, wherein the at least one sampling device is coupled to the boom; and a micro-barge towed behind the body, wherein the at least one sampling device is arranged on the micro-barge.

11. The autonomous surface vessel of claim 1, further comprising a power device that provides electrical power to the sampling system and the computer system.

12. The autonomous surface vessel of claim 1, wherein the at least one sampling device further includes a container seal arranged within an interior of the storage container at or near a second end;

wherein the end cap is configured to hermetically seal the at least one sampling device in order to preclude oxygen from entering the storage container so that the sampling material is hermetically sealed within the storage container when the at least one sampling device is in the stowed state; and wherein the housing is made of an opaque material.

13. A method of obtaining hydrocarbon samples, comprising:

deploying an autonomous surface vessel (ASV) onto a body of water, the ASV including a sampling system having one or more sampling devices, wherein each sampling device includes:

a housing including a storage container;

a sampling material receivable within the storage container;

an actuation system operatively coupled to the sampling material via a lead line; and an end cap operatively coupled to the lead line and matable with an open end of the storage container;

operating the actuation system to deploy the sampling material from the storage container of one of the sampling devices;

dragging the sampling material across a surface of the body of water and thereby capturing a sample of a waterborne hydrocarbon on the surface of the body of water;

operating the actuation system to retrieve the sampling material back into the storage container; and sealing the sampling material within storage container with the end cap sealingly engaged to the open end.

14. The method of claim 13, wherein the ASV further includes a measurement device in communication with a computer system and the measurement device includes one or more sensors, and wherein operating the actuation system to deploy the sampling material is preceded by detecting the waterborne hydrocarbon on the surface of the body of water with the one or more sensors; and further comprising autonomously operating the actuation system as directed by the computer system once the waterborne hydrocarbon is detected.

15. The method of claim 14, further comprising:

remotely communicating with the computer system; and providing command signals to the actuation system from the computer system based on remote communication with the computer system once the waterborne hydrocarbon is detected.

16. The method of claim 13, wherein the actuation system comprises a motor and a spool operatively coupled to the motor and the lead line is wound around the spool; and wherein operating the actuation system to deploy the sampling material comprises:

rotating the spool to unwind the lead line from the spool;

dislodging the end cap from the open end; and discharging the sampling material out of the storage container and into contact with the surface of the body of water.

17. The method of claim 16, wherein operating the actuation system to retrieve the sampling material comprises:

rotating the spool to wind the lead line onto the spool;

drawing the sampling material back into the storage container; and urging the end cap against the open end to sealing engage the open end.

18. The method of claim 13, wherein sealing the sampling material within storage container comprises generating a hermetic seal with the end cap and thereby preventing an influx of oxygen into the storage container.

19. A hydrocarbon sampling system, comprising:

one or more sampling devices, each sampling device including:

a housing including a storage container;

a sampling material receivable within the storage container;

an actuation system operatively coupled to the sampling material via a lead line, the actuation system comprising a motor and a spool operatively coupled to the motor via a drive shaft; and an end cap operatively coupled to the lead line and matable with an open end of the storage container, wherein the lead line is wound around the spool and actuation of the motor progressively winds the lead line onto the spool or feeds the lead line from the spool and thereby acts on the sampling material and the end cap, wherein each sampling device is actuatable between a stowed state, where the sampling material is received within the storage container and the end cap sealingly engages the open end, and a deployed state, where the end cap is disengaged from the open end and the sampling material is drawn out of the storage container.

20. The hydrocarbon sampling system of claim 19, wherein the end cap is configured to hermetically seal the sampling device in order to preclude oxygen from entering the storage container so that the sampling material is hermetically sealed within the storage container when the sampling device is in the stowed state.

* * * * *